(12) United States Patent
Heid et al.

(10) Patent No.: US 6,890,718 B2
(45) Date of Patent: May 10, 2005

(54) EXTERNAL CONTROL REAGENTS FOR NUCLEIC ACID AMPLIFICATION

(75) Inventors: Christian A. Heid, San Mateo, CA (US); Kenneth J. Livak, San Jose, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/099,738

(22) Filed: Mar. 15, 2002

(65) Prior Publication Data

US 2003/0027179 A1 Feb. 6, 2003

Related U.S. Application Data

(63) Continuation of application No. 09/645,959, filed on Aug. 24, 2000, now Pat. No. 6,358,679.

(51) Int. Cl.[7] .......................... C12Q 1/68; C12P 19/34; C07H 21/02; C07H 21/04
(52) U.S. Cl. ......................... 435/6; 435/810; 435/91.2; 536/24.33; 536/24.32; 536/23.1; 536/25.32
(58) Field of Search .......................... 435/6, 91.2, 810; 536/24.33, 24.32, 23.1, 25.32

(56) References Cited

U.S. PATENT DOCUMENTS

| | | | | |
|---|---|---|---|---|
| 5,538,848 A | * | 7/1996 | Livak et al. ................. | 435/5 |
| 5,801,155 A | * | 9/1998 | Kutyavin et al. ............ | 514/44 |
| 5,804,375 A | | 9/1998 | Gelfand et al. | |
| 5,952,202 A | * | 9/1999 | Aoyagi et al. ............. | 435/91.2 |
| 6,232,075 B1 | * | 5/2001 | William et al. ............. | 435/6 |

FOREIGN PATENT DOCUMENTS

EP        0 972 848 A2      1/2000

OTHER PUBLICATIONS

F. L. Dumoulin et al., "Semi–quantification of Human C–C Chemokine mRNAs with Reverse Transcription/Real–time PCR Using Multi–specific Standards" Journal of Immunological Methods, vol. 241, Jul. 31, 2000, pp. 109–119.

I. Afonina et al., "Efficient Priming of PCR with Short Oligonucleotides Conjugated to a Minor Groove Binder" Nucleic Acids Research, vol. 25, No. 13, 1997, pp. 2657–2660.

Coen, Donald M., "Quantification of DNAs by the Polymerase Chain Reaction Using an Internal Control, 'The Polymerase Chain Reaction'" pp. 89–96 (1994).

Corey, E. et al., "Improved Reverse Transcriptase–Polymerase Chain Reaction Protocol with Exogenous Internal Competitive Control for Prostate–Specific Antigen mRNA in Blood and Bone Marrow," Clinical Chemistry, 43:3, pp. 443–452 (1997).

Gibson, et al., "A Novel Method for Real Time Quantitative RT–PCR," Genome Research, 6:995–1001 (1996).

Gilles, et al., "Single Nucleotide Polymorphic Discrimination by an Electronic Dot Blot Assay on Semiconductor Microchips," Nature Biotechnology, vol. 17, pp. 365–370 (1990).

Heid, et al., "Real Time Quantitative PCR," Genome Research, 6:986–994 (1996).

Livak, Kenneth J., "Allelic Discrimination Using Fluorogenic Probes and the 5' Nuclease Assay," Genetic Analysis: Biomolecular Engineering, 14:143–149 (1999).

Reischl, et al., "Quantitative PCR A Survey of the Present Technology," Molecular Biotechnology, vol. 3, pp. 55–71 (1995).

"Primer Express Version 1.5 and TaqMan MGB Probes for Allelic Discrimination," User Bulletin, Applied Biosystems, pp. 1–28, May 26, 2000.

"TaqMan® Allelic Discrimination Demonstration Kit," Protocol, PE Applied Biosystems, pp. 1–35 (1998).

* cited by examiner

Primary Examiner—Kenneth R. Horlick
Assistant Examiner—Joyce Tung
(74) Attorney, Agent, or Firm—Alex Andrus; Andrew K. Finn

(57) ABSTRACT

External control reagents for nucleic acid amplification are provided that verify the absence or presence of specific target sequences, and correct primers and probes. A single-stranded, external control polynucleotide is amplified with primers of the same sequence as target primers. Probes with detectable labels and sequences specific for target and external control polynucleotides allow for detection and measurement. The primers and the detectable probe are adjacent or substantially adjacent when hybridized to the external control polynucleotide. Target and control amplicons may be detected by increased fluorescence induced by polymerase-mediated 5' nuclease cleavage or hybridization of a self-quenching probe complementary to both target and external control polynucleotides. A kit of PCR reagents can be dispensed into vessels for rapid and accurate nucleic acid amplification assay, with real-time or end-point measurements. The amplification control reagents, kits, and methods of the present invention provide positive and negative control tests which can be conducted concurrently with target amplification. Allelic differences at genetic loci can be detected, including single nucleotide polymorphisms (SNP).

31 Claims, 8 Drawing Sheets

| NTC A1 | ECP1 B1 | UNK C1 | UNK D1 | UNK E1 | UNK F1 | UNK G1 | UNK H1 |
| NTC A2 | ECP1 B2 | UNK C2 | UNK D2 | UNK E2 | UNK F2 | UNK G2 | UNK I2 |
| NTC A3 | ECP1 B3 | UNK C3 | UNK D3 | UNK E3 | UNK F3 | UNK G3 | UNK H3 |
| NTC A4 | ECP1 B4 | UNK C4 | UNK D4 | UNK E4 | UNK F4 | UNK G4 | UNK H4 |
| NTC A5 | ECP2 B5 | UNK C5 | UNK D5 | UNK E5 | UNK F5 | UNK G5 | UNK H5 |
| NTC A6 | ECP2 B6 | UNK C6 | UNK D6 | UNK E6 | UNK F6 | UNK G6 | UNK H6 |
| NTC A7 | ECP2 B7 | UNK C7 | UNK D7 | UNK E7 | UNK F7 | UNK G7 | UNK H7 |
| NTC A8 | ECP2 B8 | UNK C8 | UNK D8 | UNK E8 | UNK F8 | UNK G8 | UNK I8 |
| ECP1 A9 | ECP2 B9 | UNK C9 | UNK D9 | UNK E9 | UNK F9 | UNK G9 | UNK H9 |
| ECP1 A10 | ECP2 B10 | UNK C10 | UNK D10 | UNK E10 | UNK F10 | UNK G10 | UNK I10 |
| ECP1 A11 | ECP2 B11 | UNK C11 | UNK D11 | UNK E11 | UNK F11 | UNK G11 | UNK I11 |
| ECP1 A12 | ECP2 B12 | UNK C12 | UNK D12 | UNK E12 | UNK F12 | UNK G12 | UNK H12 |

Figure 5

EXTERNAL CONTROL REAGENTS FOR NUCLEIC ACID AMPLIFICATION

This non-provisional application is a continuation of application Ser. No. 09/645,959, filed on Aug. 24, 2000, now U.S. Pat. No. 6,358,679, which is incorporated herein by reference.

I. FIELD OF THE INVENTION

The invention relates generally to the field of nucleic acid amplification, including methods of external controls that verify the absence or presence of specific target sequences during the polymerase chain reaction by detection of amplicons.

II. BACKGROUND OF THE INVENTION

Nucleic acid amplification, and the polymerase chain reaction (PCR) in particular, is an important research tool, with applications in cloning, analysis of genetic expression, DNA sequencing, genetic mapping, drug discovery, and the like (Gilliland etal, (1990) Proc. Natl. Acad. Sci., 87:2725–2729; Bevan etal, (1992) PCR Methods and Applications, 1:222–228; Green etal, (1991) PCR Methods and Applications, 1:77–90). Descriptions of, and guidance for conducting, PCR are provided in extensive literature (Innis etal, (1989) in *PCR Protocols*, Academic Press, NY; McPherson etal, (1991) in *PCR: A Practical Approach, Volume* 1, Oxford University Press, Oxford, pp. 46, 199; McPherson etal, (1995) in *PCR 2: A Practical Approach* Oxford University Press, Oxford, pp. 7, 19).

PCR assays that discriminate and identify alleles are important to genotype DNA samples for specific mutations (Livak (1999) Genetic Analysis: Biomolecular Engineering, 14:143–49; Mein etal (2000) Genome Research, 10:330–43). PCR assays also provide relative quantification of gene expression (Gibson etal (1996) Genome Research, 6:995–1001; Heid etal (1996) Genome Research, 6:986–94; Yang etal (1993) Anal. Biochem. 208:110–16; Germer etal (1999) Genome Research, 9:72–78).

Fluorescence-based approaches to provide end-point or real-time measurements of PCR amplification products (amplicons) (Holland etal, (1991) Proc. Natl. Acad. Sci., 88:7276–80) have either employed intercalating dyes, e.g. ethidium bromide, to indicate the amount of double stranded DNA present (Gelfand etal, U.S. Pat. No. 5,210,015) or probes containing reporter-quencher pairs ("TaqMan®", 5' nuclease assay) that are cleaved during amplification to release a fluorescent signal proportional to the amount of double stranded DNA present (Livak etal, U.S. Pat. No. 5,538,848; Gelfand etal, U.S. Pat. No. 5,804,375).

Parallel control tests that confirm conditions for amplification of the target are desirable. PCR is often plagued by false positives due to template contamination from adjacent wells, pipetting errors, or aerosol transmission, especially in high density or high-throughput formats, such as 96-, 384-well, or higher density microtitre plate, or other array configurations. In addition, PCR suffers from false negative results when enzyme inhibitors are present in the target samples or when reagents are missing or degraded. Control amplification reactions are desirable for (i) normalization of quantification results, (ii) detection of amplification inhibitors in the target and other reagents, and (iii) to establish background signal levels. Positive amplification control tests for PCR give a detectable amplicon derived from a control template that is separate and distinct from the target. Detection of the positive control amplicon indicates that amplification is viable and operative within the reaction chamber. Positive amplification control tests which give no detectable product from the control components, indicate conditions within the reaction chamber that do not allow amplification, such as contaminants that inhibit PCR.

Internal control PCR is conducted in the same vessel, concurrently with PCR of the target sample polynucleotide (Coen, D. "Quantification of DNAs by the Polymerase Chain Reaction Using an Internal Control" in *The Polymerase Chain Reaction* (1994) Mullis etal, Eds., Birkhauser, Boston, Mass., pp. 89–96; Coen, D. "Quantitation of rare DNAs by polymerase chain reaction" in *Current Protocols in Molecular Biology* (1990) Ausubel, etal, Eds. Greene Publ. Assoc. and Wiley-Interscience). Amplification of an internal control polynucleotide (ICP) with primers common to the target polynucleotide and the internal control polynucleotide, gives verification of true or false negatives, i.e. if target is not detected (Gibson etal (1996) Genome Research 6:995–1001). An ICP is often an endogenous region of the target polynucleotide sample, i.e. from the same source, genome, chromosome, gene, plasmid, or fragment as the target, thus normalizing for variation in the amount of target polynucleotide. An ICP may be an endogenous RNA or DNA sequence which is present in each experimental sample as isolated. An ICP may be an exogenous or foreign sequence of RNA or DNA which is spiked in to the target sample at a known concentration. The exogenous ICP may be an in vitro construct, used to distinguish true target negatives from PCR inhibition and normalize for differences in efficiency of sample extraction cDNA synthesis (Aoyagi, U.S. Pat. No. 5,952,202).

A pervasive difficulty with internal controls is keeping amplification of the control polynucleotide from interfering with target amplification or detection of the product (Reischl etal (1995) "Quantitative PCR" in *Molecular Biotechnology*, Vol. 3, Humana Press Inc., pp.55–71). Endogenous ICP are subject to amplification inhibitors and can therefore give a false negative signal. Endogenous ICP also may have priming sites for target primers and therefore give a false positive signal. Where endogenous ICP systems share one or more primers with the target, exhaustion of the shared primers may lead to inaccurate PCR quantification and limited dynamic range. In view of the limitations and deficiencies of conventional controls for the quantification and detection of nucleic acid amplification products, non-gel based, external control PCR methods that provide positive indications of amplification are desirable.

III. SUMMARY

The present invention is directed towards novel methods, compositions and kits of reagents for detecting nucleic acid amplification of a single-stranded, external control, polynucleotide (ECP) concurrently with nucleic acid amplification of a known or unknown target polynucleotide.

In a first aspect, the invention provides a method for detecting a target polynucleotide sequence by amplifying a target polynucleotide with primer extension reagents in a first set of one or more vessels (FIG. 1A) and amplifying a single-stranded external control polynucleotide with the primer extension reagents in a second set of one or more vessels (FIG. 1B). The primer extension reagents include a forward primer, a reverse primer, one or more detectable probes, a polymerase, and one or more deoxynucleotide 5'-triphosphates (dNTP). The target polynucleotide, and the ECP and its complement contain sequences complementary to the primers and are amplified by the same forward and reverse primers during a PCR assay.

The forward primer and the detectable probe are adjacent or substantially adjacent when hybridized to the single-stranded external control polynucleotide, or its complement. Also, the reverse primer and the detectable probe are adjacent or substantially adjacent when hybridized to the single-stranded external control polynucleotide, or its complement. Signals, such as fluorescence, are then detected from the detectable probes.

In one embodiment, the detectable probes are self-quenching fluorescence probes (SQP), each comprising reporter dye and quencher moieties.

The primer extension reagent of the second set of vessels may include a first detectable probe and a second detectable probe. The sequence of the first probe differs from the second probe by one or more mismatches, insertions, or deletions. The signal from the first probe is resolvable from the signal of the second probe.

In another embodiment, a third set of one or more vessels includes a second single-stranded ECP and primer extension reagents. The sequence of the first single-stranded ECP differs from the second single-stranded ECP by one or more mismatches, insertions, or deletions. The sequence portion of the first single-stranded ECP complementary to a detectable probe differs by a single nucleotide from the sequence portion of the second single-stranded ECP complementary to the detectable probe.

In another aspect, the invention provides kits of reagents for nucleic acid amplification comprising: a single-stranded external control polynucleotide a forward primer, a reverse primer, a nucleic acid polymerase having 5' nuclease activity, a detectable probe, one or more nucleotide 5'-triphosphates; and other primer extension reagents necessary for nucleic acid amplification. In one embodiment, the primers, self-quenching fluorescence probes, and primer extension reagents are conveniently dispensed as a kit of reagents.

IV. BRIEF DESCRIPTION OF THE DRAWINGS

FIG. 1A shows a schematic for the hybridization of primers and a detectable probe to a target polynucleotide. In this exemplary embodiment, the probe is hybridized to the sense strand.

FIG. 1B shows a schematic for the hybridization of primers and probe to an external control polynucleotide (ECP). In this exemplary embodiment, the detectable probe is hybridized to the sense strand. Gaps between primers and probe are denoted by n. Overhangs beyond primer binding sites on the ECP are denoted by o.

FIG. 5 shows a plate diagram with placement of four sets of vessels for PCR reactions in a 96-well format: first—sample (UNK); second—(ECP1); third—(ECP2); and fourth—control, no template control (NTC).

V. DETAILED DESCRIPTION OF EXEMPLARY EMBODIMENTS

Figure 1A:
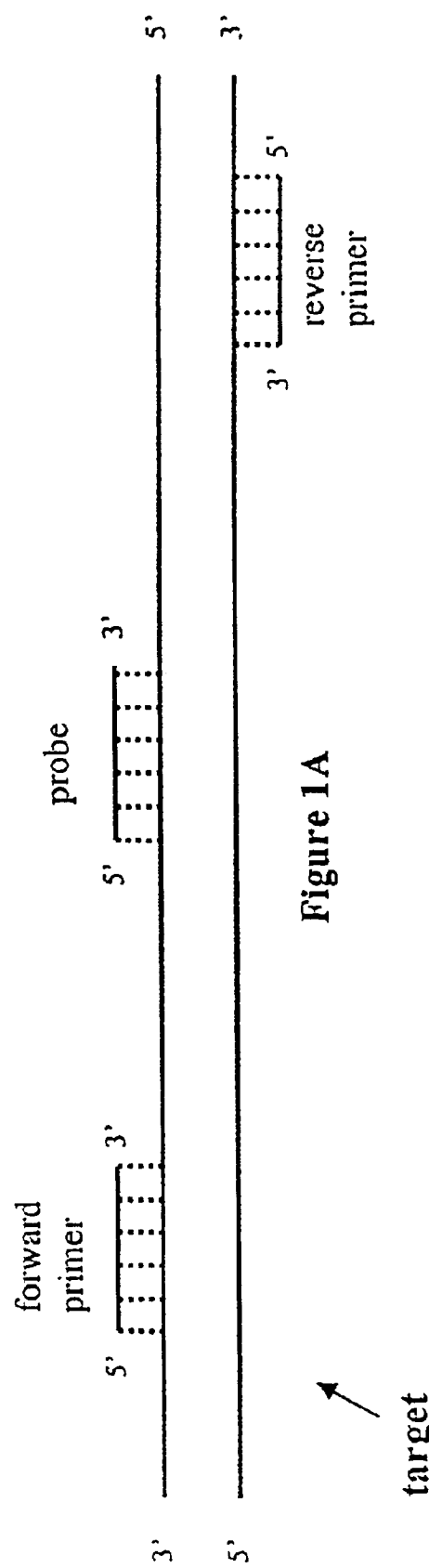

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the scope of the claimed invention.

V.1 Definitions

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine (Kutyavin etal, U.S. Pat. No. 5,912,340), inosine, nebularine, nitropyrrole, nitroindole, 2-aminopurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methyl-indole, and ethenoadenine (Fasman (1989) *Practical Handbook of Biochemistry and Molecular Biology*, pp. 385–394, CRC Press, Boca Raton, Fla.).

"Nucleoside" refers to a compound consisting of a nucleobase linked to the C-1' carbon of a ribose sugar. The ribose may be substituted or unsubstituted. Substituted ribose sugars include, but are not limited to, those riboses in which one or more of the carbon atoms, e.g., the 3'-carbon atom, is substituted with one or more of the same or different —R, —OR, —NRR or halogen groups, where each R is independently —H, $C_1$–$C_6$ alkyl or $C_5$–$C_{14}$ aryl. Riboses include ribose, 2'-deoxyribose, 2',3'-dideoxyribose, 3'-haloribose, 3'-fluororibose, 3'-chlororibose, 3'-alkylribose, e.g. 2'-O-methyl, 4'-α-anomeric nucleotides, 1'-α-anomeric nucleotides, and 2'-4'-linked and other "locked", bicyclic sugar modifications (Wengel, etal WO 99/14226). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication*, $2^{nd}$ Ed., Freeman, San Francisco, Calif.).

"Nucleotide" refers to a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "oligonucleotide" and "polynucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and sugar analogs. Polynucleotides typically range in size from a few monomeric units, e.g. 5–40, when they are frequently referred to as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Attachment site" refers to a site on a moiety, e.g. a label or an oligonucleotide, which is covalently attached to a linker.

"Linker" refers to a chemical moiety comprising a covalent bond or a chain of atoms that covalently attaches a label to a polynucleotide, or one label to another.

"Alkyl" refers to a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1–12 saturated and/or unsaturated carbons, including, but not limited to, methyl, ethyl, propyl, butyl, and the like.

"Alkyldiyl" refers to a saturated or unsaturated, branched, straight chain or cyclic hydrocarbon radical of 1–20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryldiyl" refers to an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound. Typical aryldiyl groups include, but are not limited to, radicals derived from benzene, substituted benzene, naphthalene, anthracene, biphenyl, and the like.

"Reactive linking group" refers to a chemically reactive substituent or moiety, e.g. a nucleophile or electrophile, capable of reacting with another molecule to form a covalent bond in a linker.

"Heterocycle" refers to a molecule with a ring system in which one or more ring atoms is a heteroatom, e.g. nitrogen, oxygen, and sulfur (as opposed to carbon).

"Internucleotide analog" means a phosphate ester analog of an oligonucleotide such as: (i) alkylphosphonate, e.g. $C_1$–$C_4$ alkylphosphonate, especially methylphosphonate; (ii) phosphoramidate; (iii) alkylphosphotriester, e.g. $C_1$–$C_4$ alkylphosphotriester; (iv) phosphorothioate; and (v) phosphorodithioate. Internucleotide analogs also include non-phosphate analogs wherein the sugar/phosphate subunit is replaced by an a non-phosphate containing backbone structure. One type of non-phosphate oligonucleotide analogs have an amide linkage, such as a 2-aminoethylglycine unit, commonly referred to as PNA (Nielsen, etal (1991) "Sequence-selective recognition of DNA by strand displacement with a thymidine-substituted polyamide", Science 254:1497–1500).

The term "adjacent" refers to the arrangement of two oligonucleotides each hybridized to a third polynucleotide where there is no intervening nucleotide(s), or gap, between the two oligonucleotides. When the two oligonucleotides are hybridized next to each other with no gap, they are adjacent.

The term "substantially adjacent" refers to the arrangement of two oligonucleotides each hybridized to a third polynucleotide where there are 1 to 5 intervening nucleotide (s) as a gap between the two oligonucleotides.

The terms "target sequence" and "target polynucleotide" mean a polynucleotide sequence that is the subject of hybridization with a complementary polynucleotide, e.g., a primer or probe. The sequence can be composed of DNA, RNA, an analog thereof, including combinations thereof.

The term "amplicon" means a polynucleotide sequence amplified within a target sequence, and defined by the distal ends of two primer-binding sites.

The term "detectable probe" means an oligonucleotide that forms a duplex structure, or higher order structure, e.g. triple helix, by complementary base pairing with a sequence of a target nucleic acid and is capable of emitting a detectable signal. A detectable probe may be labelled with a fluorescent dye. A "self-quenching fluorescence probe" (SQP) is labelled with a pair of labels comprised of a fluorescent reporter dye and quencher which interact by energy transfer (FRET).

The term "label", as used herein, refers to any moiety which can be attached to an oligonucleotide, nucleotide or nucleotide 5'-triphosphate and that functions to: (i) provide a detectable signal; (ii) interact with a second label to modify the detectable signal provided by the first or second label, e.g. FRET; (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

The term "quenching" refers to a decrease in fluorescence of a first moiety (reporter dye) caused by a second moiety (quencher) regardless of the mechanism. The term "self-quenching" refers to an intramolecular, energy transfer effect, e.g. FRET (fluorescence resonance energy transfer), whereby a fluorescent reporter dye and quencher are joined on a probe in a configuration that permits energy transfer from the fluorophore to the quencher, resulting in a reduction of the fluorescence by the fluorescent dye. The self-quenching effect may be diminished or lost upon hybridization of the probe to its complement or upon 5' nuclease cleavage whereupon the fluorescent reporter and the quencher are separated.

The term "5' nuclease activity" refers to an enzyme activity that cleaves nucleic acid at phosphodiester bonds. This activity can be either endo (cleaves at internal phosphodiester bonds) or exo (cleaves at the phosphodiester bond closest to the 5' terminus of the nucleic acid strand.

The term "end-point analysis" refers to a method where data collection occurs only when a reaction is complete. End-point analysis of PCR entails fluorescent dye signal measurement when thermal cycling and amplification is complete. Results may be reported in terms of the change in fluorescence, i.e. fluorescence intensity units, of the fluorescent dye signal from start to finish of the PCR thermal cycling, preferably minus any internal control signals.

The term "real-time analysis" refers to periodic monitoring during PCR. Certain systems such as the ABI 7700 Sequence Detection System (Applied Biosystems, Foster City, Calif.) conduct monitoring during each thermal cycle at a pre-determined or user-defined point. Real-time analysis of the 5' nuclease assay measures fluorescent dye signal changes from cycle-to-cycle, preferably minus the change in fluorescence from a passive internal reference.

V.2 Primers, Probes and External Control Polynucleotides

It has been discovered that a single-stranded, external control polynucleotide (ECP) undergoes amplification in vessels (e.g. reaction sites, spots, tubes, chambers, wells) on a plate, set of tubes, microtitre tray, array configuration, or other arrangement for PCR reactions. The ECP-containing vessels are separate from the vessels containing known or unknown target polynucleotide. All vessel undergo concurrent thermal cycling. The control methods of the invention impart convenience in preparing and dispensing reagents in kit format, and measuring results.

The ECP and target polynucleotide are amplified in separate reaction sites (i.e. vessels, chambers, wells) with common primers and probes. The ECP sequence is selected ("designed") to be amplified by the forward and reverse primers and to comprise the detectable probe sequence or the complement to the detectable probe sequence. The ECP comprises sequences complementary to forward and reverse primer sequences and probe sequences with few if any intervening sequences. Intervening sequences are single stranded regions, or gaps, in the hybridization complex (FIGS. 1–3) denoted by n, the number of nucleotides of the ECP which are not hybridized to primers or probe. As illustrated in FIG. 1, primers should hybridize adjacent (n=0) or substantially adjacent (n=1 to about 5) to the probe on the ECP. Gap nucleotides may be arbitrarily chosen. Therefore, generally the ECP is short relative to the target amplicon.

In one embodiment of the method, the forward primer and the detectable probe are adjacent when hybridized to the single-stranded external control polynucleotide or its complement, and the reverse primer and the detectable probe are adjacent (n=0, FIGS. 1B, 2, 3) when hybridized to the single-stranded external control polynucleotide or its complement.

Figure 1B:
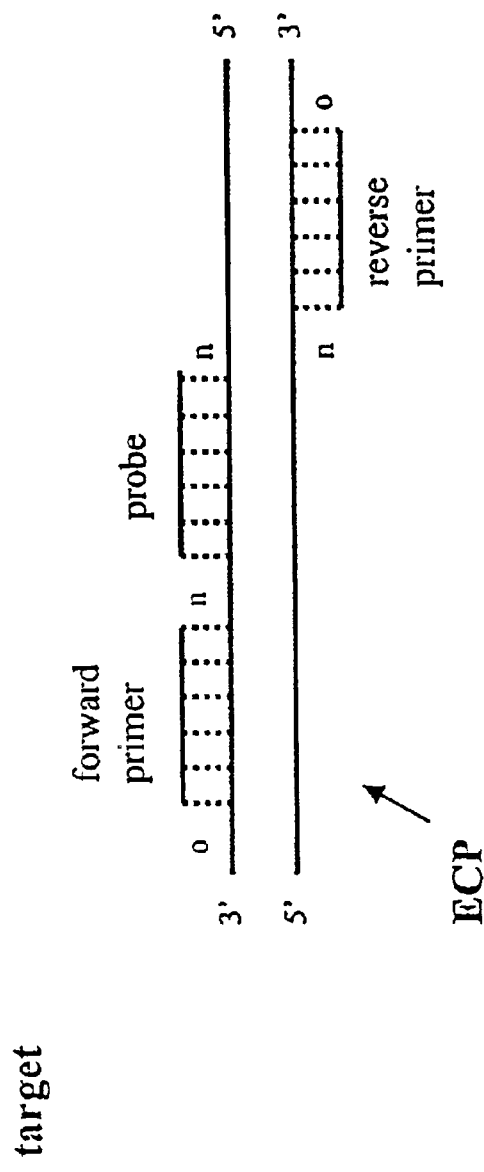
Figure 2:
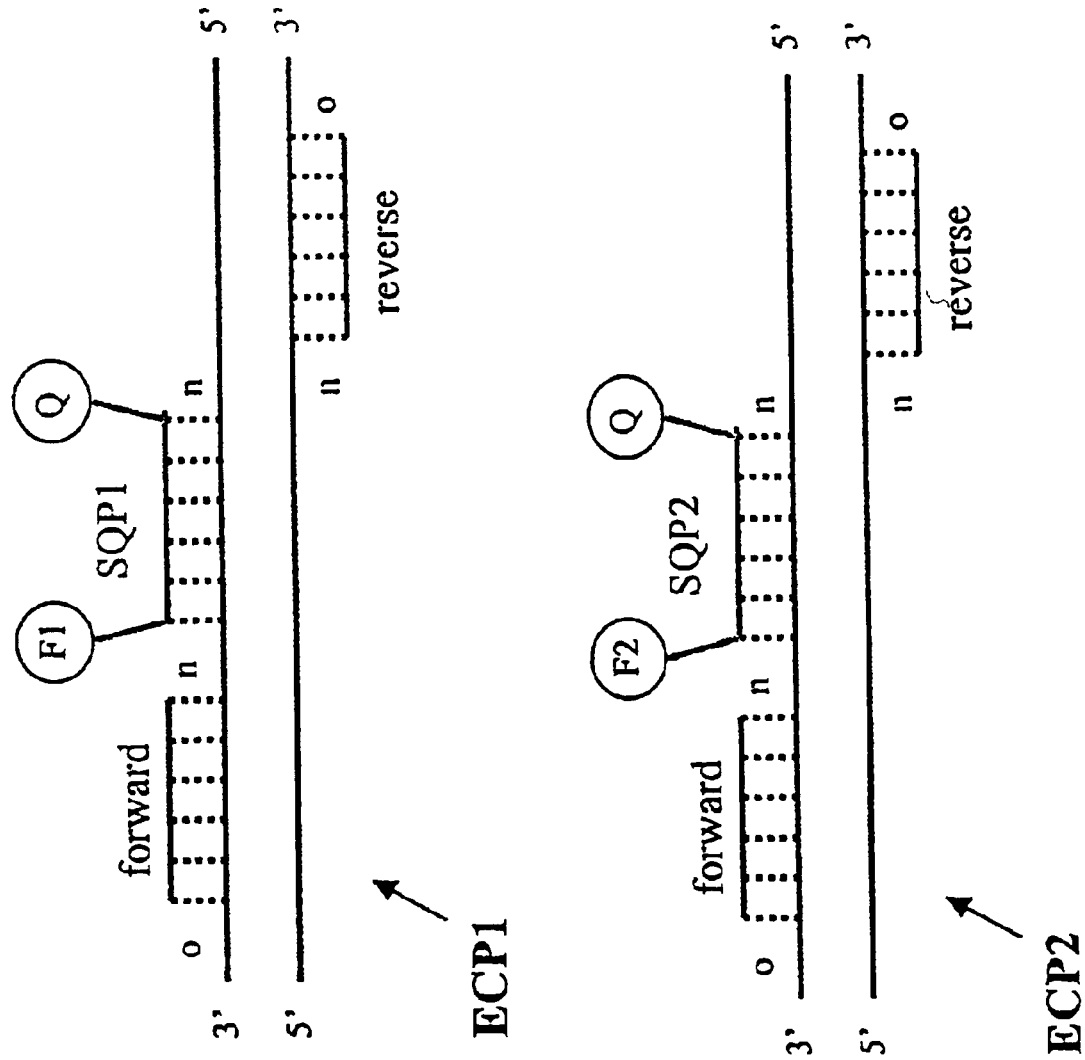
FIG. 2 shows a schematic for the hybridization of allele-specific self-quenching fluorescence probes (SQP1 and SQP2) to external control polynucleotides (ECP1 and ECP2).
Figure 3:
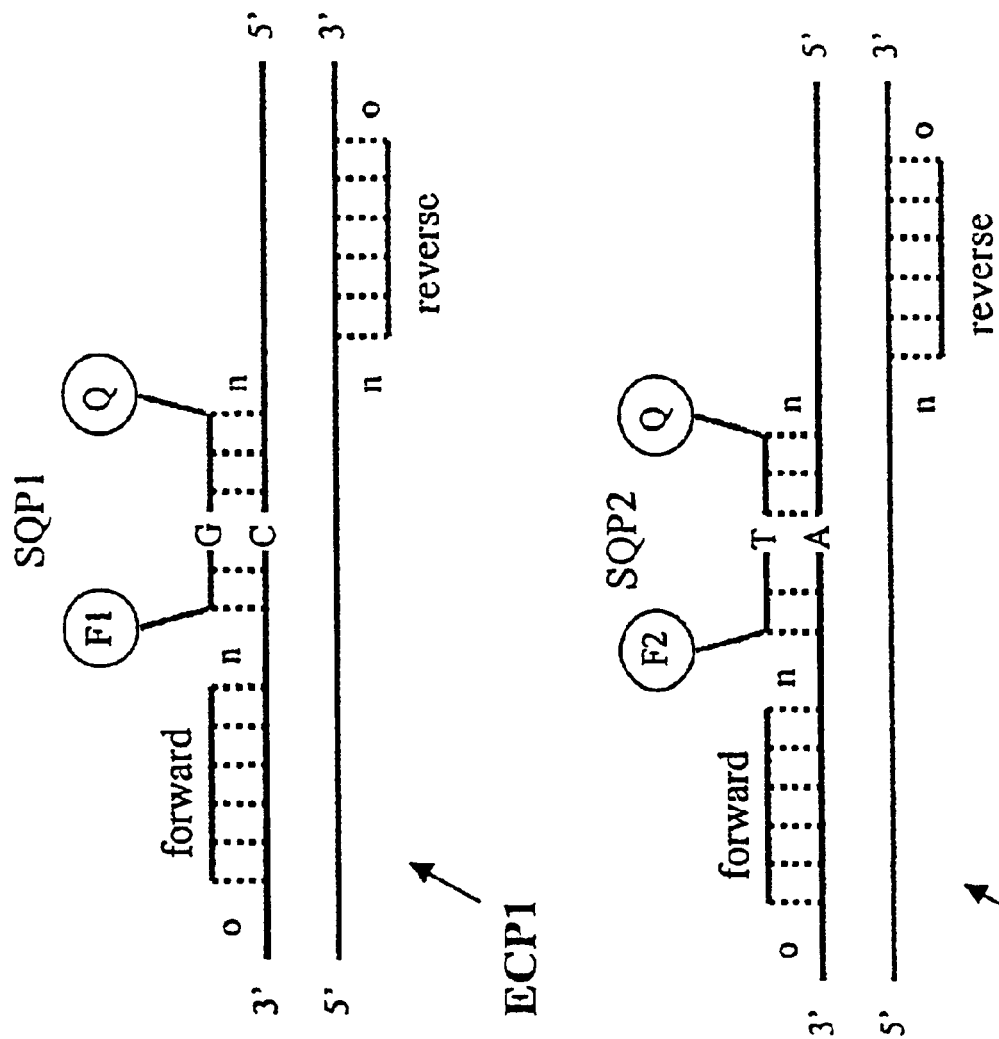
FIG. 3 shows a schematic of SQP1 hybridizing to ECP1 through a G/C base pair and SQP2 hybridizing to ECP2 through an A/T base pair at a single nucleotide polymorphic (SNP) site.

In another embodiment, the forward primer and the detectable probe are substantially adjacent, i.e. separated by a gap of 1 to about 5 nucleotides, when hybridized to the single-stranded external control polynucleotide, and the reverse primer and the detectable probe are separated by a gap of 1 to 5 nucleotides when hybridized to the single-stranded external control polynucleotide (n=1–5, FIGS. 1B, 2, 3). The single-stranded external control polynucleotide forms single-stranded overhangs (designated as o in FIGS. 1B, 2, 3) of 1 to about 10 nucleotides when hybridized to the forward primer and the reverse primer. Alternatively, the ECP and a primer may form a blunt end (o=0).

The forward primer, reverse primer and detectable probe are DNA oligonucleotides and may each be 10 to 40 nucleotides in length The primers, probes, and ECP may contain nucleotide analogs, including modifications to a sugar, a nucleobase, or an internucleotide linkage.

An additional aspect of the invention is that the ECP begins the amplification process as a single-stranded polynucleotide. During PCR, the complementary strand of the ECP is formed and the ECP then participates like any double-stranded DNA in the steps of melting, annealing, and primer extension. One primer, forward or reverse, hybridizes to the single-stranded external control polynucleotide and the other hybridizes to its complement, in a manner which allows amplification to occur. The complement of the single-stranded ECP is formed during PCR. The combined aspects of short length and single-strandedness allows the ECP to be synthesized by automated synthesis in an economical fashion, with great efficiency, accuracy and minimal labor requirement since shorter oligonucleotides are made in higher yield and higher purity. Additionally, short amplicons in the range of 50–150 bp are amplified with high efficiency. ECP are typically 30–110 nt, encompassing the sequences of the forward and reverse primers, and detectable probe.

Detectable probes may be designed with a G-C content in the range of 20–80%. Contiguous sequences in the probe of four or more G nucleotides are preferably avoided to minimize non-Watson/Crick base-pairing interactions, such as base stacking structures. The presence of G at the 5' end is preferably avoided to prevent self-quenching of a 5' fluorescent dye with a 5' G. The strand (sense or antisense) of the probe may be selected on the basis of which sequence has more C than G nucleotides. Using the Primer Express™ software (Applied Biosystems), probe sequences for the 5' nuclease assay are selected to have melting temperatures (Tm) from 65–67° C., but probe sequences with other Tm may be used as appropriate. A detectable probe may be designed to be complementary to the sense strand of the target polynucleotide or ECP, which also hybridizes to the forward primer, e.g. see FIGS. 1A and 1B. Alternatively, the probe may be designed to be complementary to the antisense strand of the target polynucleotide or ECP.

The nucleic acid amplification of the target polynucleotide and the external control polynucleotide may be measured by fluorescence detection of reporter dyes from a self-quenching fluorescence probe (SQP), which includes a reporter dye and a quencher moiety. The reporter dye may be a xanthene dye, such as a fluorescein dye. The reporter dye is typically separated from the quencher by at least 12 nucleotides (nt). The reporter dye may be attached at the 5' terminus or 3' terminus of the self-quenching fluorescence probe and the quencher attached at the opposite terminus of the self-quenching fluorescence probe. For example, the SQP may be labelled at the 5' nucleotide with a fluorescent reporter dye and at the 3' nucleotide with a quencher. The quencher may be non-fluorescent, to aid spectral resolution of the reporter dyes. Alternatively, the quencher may be fluorescent so as to be detectable. The self-quenching fluorescence probe may also be labelled with a minor groove binder. Where the probe is labelled with a minor groove binder or is comprised of nucleotide analogs that increase specificity (higher Tm) relative to DNA probes, the probe may be shorter, e.g. less than 12 nt. Preferably, the sequences of two or more allelic self-quenching probes (SQP) are selected to have the same, or approximately the same, Tm.

An SQP may have a region of self-complementarity which allows the probe to exist in a quenched hairpin conformation when not bound to complementary target polynucleotide or ECP (see for example, Tyagi etal U.S. Pat. No. 5,925,517). When hairpin self-quenching fluorescence probes form a duplex with target polynucleotide or ECP, the fluorescent dye and the quencher are spatially separated and quenching is precluded or significantly minimized, resulting in an increase in fluorescence.

Primer sequences may be selected to have Tm from 58–60° C. but primer sequences with other Tm may be used as appropriate. Depending on reaction conditions, the primer Tm may be higher or lower. Like probe selection, contiguous sequences in the probe of four or more Gs are preferably avoided. The five nucleotides at the 3' end should have no more than two G and/or C bases. The length of primers and probes are typically 12–40 nt.

For certain applications, e.g. allelic detection, the amplicon of the target polynucleotide is designed to have a polymorphic site approximately in the middle of the probe region, and most sensitive, i.e. highest specificity, for discrimination by detectable probes.

V.2A Oligonucleotide Synthesis

Oligonucleotides are commonly synthesized on solid supports by the phosphoramidite method (U.S. Pat. Nos. 4,415,732; 4,973,679; 4,458,066; Beaucage, S. and Iyer, R. (1992) Tetrahedron 48:2223–2311) using commercially available phosphoramidite nucleosides, supports e.g. silica, controlled-pore-glass (U.S. Pat. No. 4,458,066) and polystyrene (U.S. Pat. Nos. 5,047,524 and 5,262,530) and automated synthesizers (Models 392, 394, 3948 DNA/RNA Synthesizers, Applied Biosystems).

V.2B Oligonucleotide Labelling

Labelling can be accomplished using any one of a large number of known techniques employing known labels, linkages, linking groups, reagents, reaction conditions, and analysis and purification methods. Generally, and depending upon the particular application, the linkage linking a label and an oligonucleotide or nucleotide should not (i) interfere with primer extension, (ii) inhibit polymerase activity, or (iii) adversely affect the fluorescence properties of a dye, e.g. quenching or bleaching. Exemplary labels include lightemitting compounds which generate a detectable signal by fluorescence, chemiluminescence, or bioluminescence (Kricka, L. in *Nonisotopic DNA Probe Techniques* (1992), Academic Press, San Diego, pp. 3–28). Another class of labels are hybridization-stabilizing moieties that serve to enhance, stabilize, or influence hybridization of duplexes, e.g. intercalators, minor-groove binders, and cross-linking functional groups (Blackburn, G. and Gait, M. Eds. "DNA and RNA structure" in *Nucleic Acids in Chemistry and Biology*, $2^{nd}$ Edition, (1996) Oxford University Press, pp. 15–81). Yet another useful class of labels serve to effect the separation or immobilization of a molecule by specific or non-specific capture means (Andrus, A. "Chemical methods for 5' non-isotopic labelling of PCR probes and primers" (1995) in *PCR 2: A Practical Approach*, Oxford University Press, Oxford, pp. 39–54).

Labelling typically results from mixing an appropriate reactive label and an oligonucleotide in a suitable solvent in which both are soluble, using methods well-known in the art to effect a covalent bond forming reaction (Hermanson, *Bioconjugate Techniques*, (1996) Academic Press, San Diego, Calif. pp. 40–55, 643–71), followed by separation of the labelled oligonucleotide from any starting materials or unwanted by-products. The labelled oligonucleotide can be stored dry or in solution for later use, preferably at low temperature.

The reactive label may include a reactive linking group at one of the substituent positions, e.g. 5- or 6-carboxyl of fluorescein or rhodamine, for covalent attachment to an oligonucleotide. Reactive linking groups may be electrophilic functional groups capable of reacting with nucleophilic groups on an oligonucleotide, such as an hydroxyl, an amine or a thiol. Examples of reactive linking groups include succinimidyl ester, isothiocyanate, sulfonyl chloride, sulfonate ester, silyl halide, 2,6-dichlorotriazinyl, pentafluorophenyl ester, phosphoramidite, maleimide, haloacetyl, epoxide, alkyl halide, allyl halide, aldehyde, ketone, acylazide, anhydride, and iodoacetamide.

One reactive linking group of a label is an N-hydroxysuccinimidyl ester (NHS), e.g. the NHS of a carboxyl group substituent of a fluorescent dye. The NHS ester of the dye may be preformed, isolated, purified, and/or characterized, or it may be formed in situ and reacted with a nucleophilic group of an oligonucleotide. Typically, a carboxyl form of the dye is activated by reacting with some combination of the following reagents to give the NHS ester of the dye: (i) a carbodiimide reagent, e.g. dicyclohexylcarbodiimide, diisopropylcarbodiimide, or a uronium reagent, e.g. TSTU (O-(N-Succinimidyl)-N,N,N', N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), (ii) an activator, such as 1-hydroxybenzotriazole (HOBt), and (iii) N-hydroxysuccinimide.

Another reactive linking group of a label is a phosphoramidite form of fluorescent dyes, quenchers, minor groove binders, and mobility modifiers. Phosphoramidite dye reagents are particularly useful for the automated synthesis of labelled oligonucleotides. The phosphoramidite reagents can be nucleosidic or non-nucleosidic. Phosphoramidite dye reagents, nucleosidic and non-nucleosidic, allow for labelling at other sites of an oligonucleotide, e.g. 5' and 3' terminii, nucleobase, internucleotide linkage, sugar (U.S. Pat. Nos. 5,736,626; 5,141,813). Labelling at the nucleobase, internucleotide linkage, and sugar sites allows for internal and multiple labels on the oligonucleotide. In some instances, the label may contain functional groups that require protection either during the synthesis of the phosphoramidite reagent or during its subsequent use to label molecules such as oligonucleotides, e.g. phenolic oxygen atoms of fluorescein dyes. The protecting group(s) used will depend upon the nature of the functional groups, and will be apparent to those having skill in the art (Greene, T. and Wuts, P. *Protective Groups in Organic Synthesis*, 2nd Ed., John Wiley & Sons, New York, 1991).

Oligonucleotide primers and probes of the present invention may be labelled with moieties that affect the rate of electrophoretic migration, i.e. mobility-modifying labels. Mobility-modifying labels include, but are not limited to biotin, cholesterol, and polyethyleneoxy units, $-(CH_2CH_2O)_n-$ where n may be 1 to 100, and typically from 2 to 20 (e.g., U.S. Pat. No. 5,624,800). The polyethyleneoxy (PEO) units may be interspersed with phosphate groups. Specifically labelling fluorescent-labelled primers with additional labels of polyethyleneoxy of discrete and known size allows for separation by electrophoresis of amplicons, substantially independent of the size, i.e. number of nucleotides, of the amplicon. That is, polynucleotides of the same length may be discriminated upon the bases of spectrally resolvable dye labels and mobility-modifying labels. Polynucleotides bearing both dye labels and mobility-modifying labels may be formed enzymatically by ligation or polymerase extension of the single-labelled oligonucleotide or nucleotide constituents. The PEO label may be comprised of charged groups, such as phosphodiester to impart charge and increase electrophoretic mobility (velocity). The PEO label may be uncharged and act to retard electrophoretic mobility. Such modifiers may serve to influence or normalize the electrophoretic velocity of a set of amplicons during analysis, e.g. by fluorescent detection, to improve resolution and separation (U.S. Pat. No. 5,470,705)

One class of labels provide a signal for detection of labelled extension products by fluorescence, chemiluminescence, and electrochemical luminescence (Kricka, L. in *Nonisotopic DNA Probe Techniques* (1992), Academic Press, San Diego, pp. 3–28). Chemiluminescent labels include 1,2-dioxetane compounds (U.S. Pat. No. 4,931,223; Bronstein, etal (1994) "Chemiluminescent and bioluminescent reporter gene assays", Anal. Biochemistry 219:169–81).

Figure 4A:
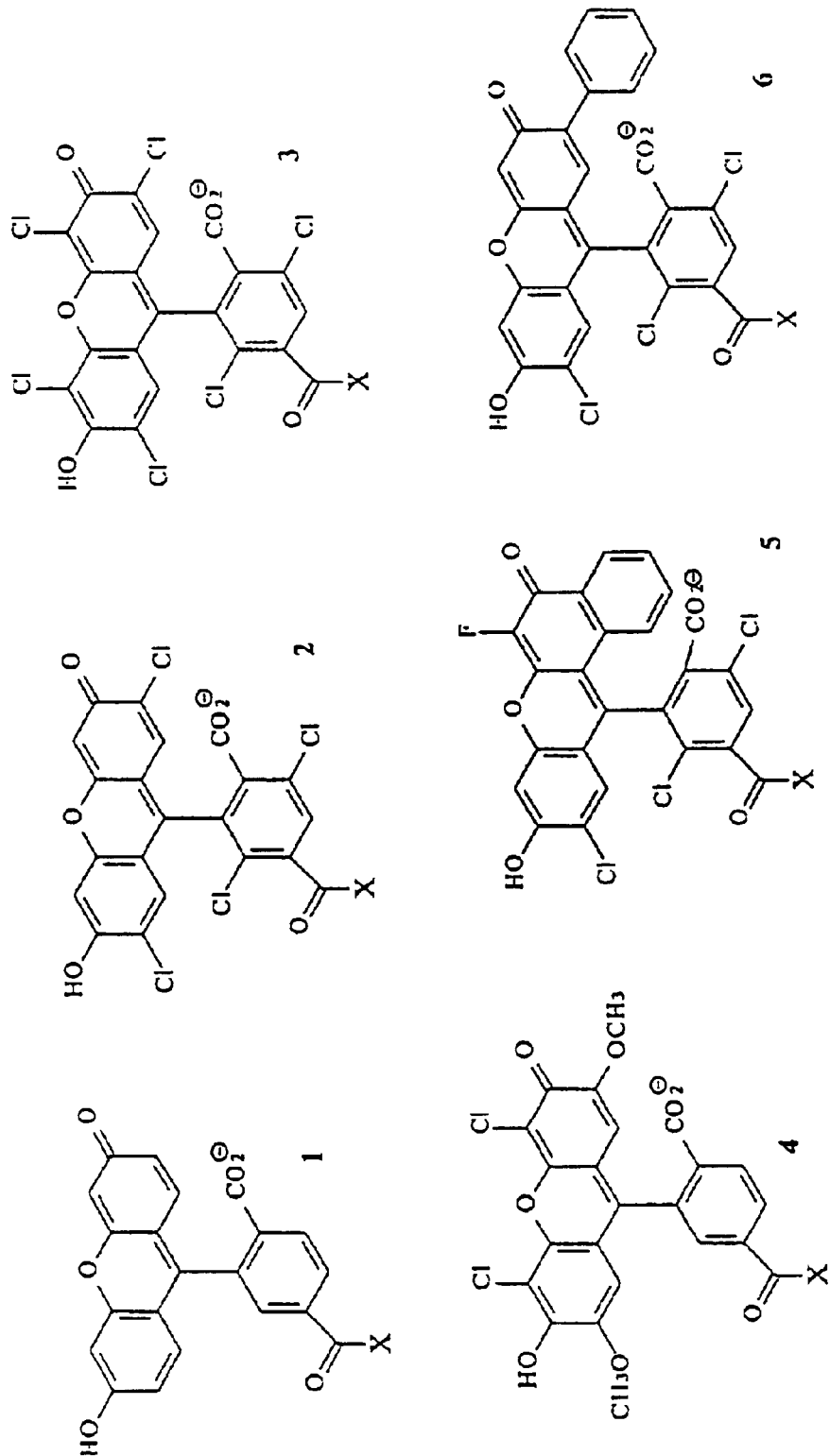
FIG. 4A shows the structures of exemplary fluorescent reporter dye labels in self-quenching probes. X is an attachment site to the probe.

Fluorescent dyes useful for labelling probes, primers, and nucleotide 5'-triphosphates include fluoresceins, rhodamines (e.g., U.S. Pat. Nos. 5,366,860; 5,936,087; 6,051,719), cyanines (U.S. Pat. No. 6,080,868 and WO 97/45539), and metal porphyrin complexes (WO 88/04777). Examples of fluorescein dyes include 6-carboxyfluorescein (6-FAM) 1, 2',4',1,4,-tetrachlorofluorescein (TET) 2 and 2',4',5',7',1,4-hexachlorofluorescein (HEX) 3 (U.S. Pat. No. 5,654,442), 2',7'-dimethoxy-4',5'-dichloro-6-carboxyrhodamine (JOE) 4, 2'-chloro-5'-fluoro-7',8'-fused phenyl-1,4-dichloro-6-carboxyfluorescein 5 (U.S. Pat. Nos. 5,188,934 and 5,885,778), 2'-chloro-7'-phenyl-1,4-dichloro-6-carboxyfluorescein 6 (U.S. Pat. No. 6,008,379 (FIG. 4A). The 5-carboxyl, and other regio-isomers, may also have useful detection properties. Fluorescein and rhodamine dyes may have 1,4-dichloro substituents (bottom ring as shown, FIG. 4A).

Figure 4B:
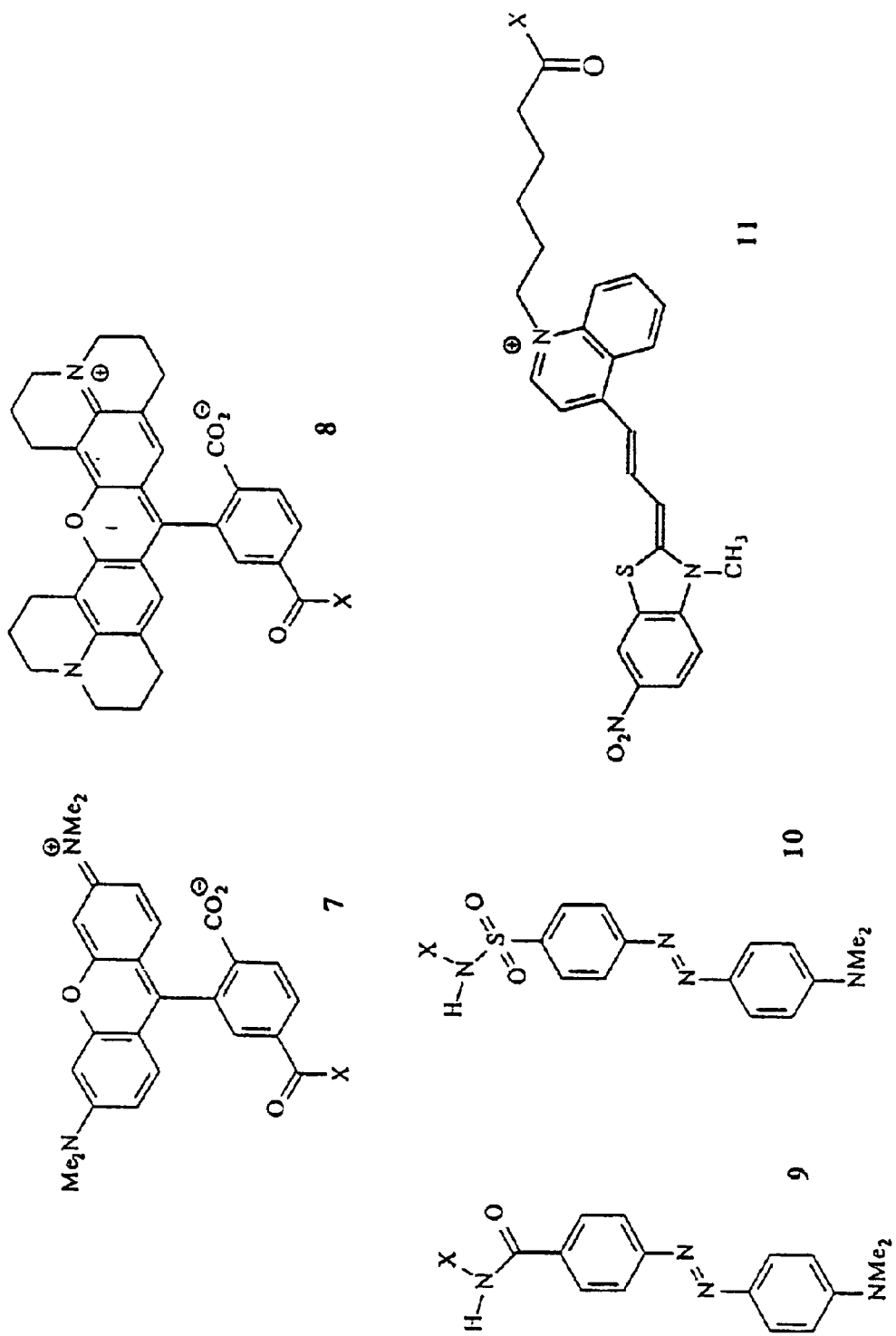
FIG. 4B shows the structures of exemplary quencher labels in self-quenching probes. X is an attachment site to the probe.

Another class of probe labels include fluorescence quencher moieties. The emission spectra of a quencher overlaps with an intermolecular fluorescent dye such that the fluorescence of the fluorescent dye is substantially diminished, or quenched, by the phenomena of fluorescence resonance energy transfer "FRET" (Clegg, R., (1992) Meth. Enzymol., 211:353–388). Quenchers include, but are not limited to, (i) rhodamine fluorescent dyes selected from the group consisting of tetramethyl-6-carboxyrhodamine (TAMRA) 7, tetrapropano-6-carboxyrhodamine (ROX) 8, and (ii) diazo compounds, e.g. 9–11, and (iii) cyanine dyes including 11, anthraquinone, malachite green, nitrothiazole, and nitroimidazole compounds and the like (FIG. 4B). Some nitro-substituted forms of quenchers are effective quenchers (Lee etal, U.S. Pat. No. 6,080,868). Non-fluorescent quencher moieties may allow for better spectral discrimination between the reporter dyes.

Another class of labels serve to effect the separation or immobilization of labelled primer extension products by specific or non-specific capture means, e.g. biotin; 2,4-dinitrophenyl (DNP); and digoxigenin (Andrus, A. "Chemical methods for 5' non-isotopic labelling of PCR probes and primers" (1995) in PCR 2: A Practical Approach, Oxford University Press, Oxford, pp. 39–54).

Another class of probe and primer labels, referred to herein as hybridization-stabilizers, include but are not limited to minor groove binders (MGB), intercalators, polycations, such as poly-lysine and spermine, and crosslinking functional groups. Hybridization-stabilizers may increase the stability of base-pairing, i.e. affinity, or the rate of hybridization (Corey, (1995) J. Amer. Chem. Soc. 117:9373–74) of the primer or probe and the target polynucleotide. Hybridization-stabilizers serve to increase the specificity of base-pairing, exemplified by large differences in Tm (ΔTm) between perfectly complementary sequences and where the resulting duplex contains one or more mismatches of Watson/Crick base-pairing (Blackburn, G. and Gait, M. Eds. "DNA and RNA structure" in *Nucleic Acids in Chemistry and Biology*, $2^{nd}$ Edition, (1996) Oxford University Press, pp. 15–81 and 337–46). Minor groove binders include, but are not limited to, Hoechst 33258 (Rajur, etal (1997) J. Organic Chem. 62:523–29), $CDPI_{1-3}$ (Kutyavin etal, U.S. Pat. Nos. 5,801,155 and 6,084,102), and MGB1 (Gong, etal (1997) Biochem. and Biophys. Res. Comm. 240:557–60). The MGB label often imparts greater affinity (higher Tm), and thus allows the use of shorter probes.

Nucleobase-labelled oligonucleotides may bear multiple labels, e.g. fluorescent dyes, attached through the nucleobases. Nucleobase-labelled oligonucleotides may be formed by: (i) enzymatic incorporation of nucleotide reagents where $R^{19}$ is triphosphate, by a DNA polymerase or ligase, and (ii) coupling of a nucleoside phosphoramidite reagent by automated synthesis. Whereas, nucleobase-labelled oligonucleotides may be multiply labelled by incorporation of more than one incorporatable nucleotide, labelling with a phosphoramidite dye label reagent leads to singly 5'-labelled oligonucleotides, according to the following formula:

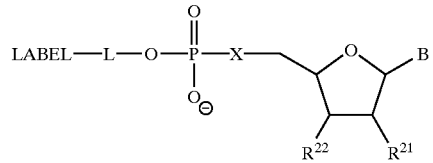

where X is O, NH, or S; $R^{21}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH{=}CH_2$; $R^{22}$ is H, phosphate, internucleotide phosphodiester, or internucleotide analog; and $R^{23}$ is H, phosphate, internucleotide phosphodiester, or internucleotide analog. L is alkyldiyl, e.g. 1,6-hexyldiyl, aryldiyl, or polyethyleneoxy (Andrus, (1995) "Chemical methods for 5' non-isotopic labelling of PCR probes and primers" in *PCR 2: A Practical Approach*, Oxford University Press, Oxford, pp. 39–54; Hermanson, *Bioconjugate Techniques*, (1996) Academic Press, San Diego, Calif. pp. 40–55, 643–71; Mullah (1998) Nucl. Acids Res. 26:1026–1031).

V.2D Nucleotide Labelling

Nucleotide 5'-triphosphates may be labelled for use in methods of the invention. Multiple incorporation of fluorescent-labelled nucleotides during PCR yields amplicons with a high degree of fluorescence intensity, increasing sensitivity of low copy number target polynucleotides. The sugar or nucleobase moieties of the nucleotides may be labelled. Nucleobase labelling sites include, but are not limited to, the 8-C of a purine nucleobase, the 7-C or 8-C of a 7-deazapurine nucleobase, and the 5-position of a pyrimidine nucleobase. The labelled nucleotide may be enzymatically incorporatable and enzymatically extendable. Labelled nucleotide 5'-triphosphates may have the following formula:

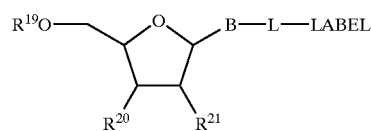

where LABEL is a protected or unprotected label, including fluorescent dye, quencher, or energy transfer dye and the like. B is a nucleobase, e.g. uracil, thymine, cytosine, adenine, 7-deazaadenine, guanine, and 8-deazaguanosine. $R^{19}$ is triphosphate, thiophosphate, or phosphate ester analog. $R^{20}$ and $R^{21}$, when taken alone, are each independently H, HO, and F. L is a linker, e.g. a bond, alkyldiyl ($C_1$–$C_{12}$), alkenyldiyl ($C_1$–$C_{12}$), or alkynyldiyl ($C_1$–$C_{12}$). One exemplary linker, L is:

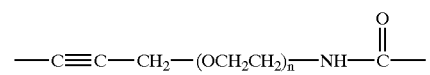

wherein n is 0, 1, or 2 (Khan etal, U.S. Pat. No. 4,757,141).

V.3 Automated PCR Analysis

The methods of the invention may be conducted on automated instrumentation designed for carrying out nucleic acid amplifications, e.g. thermal cyclers and the like. The instrumentation may include data collection and post-PCR analysis software that permits PCR to be monitored in real-time or quantitated by end-point detection. Methods of the invention include homogeneous PCR assays where reaction chambers remain closed during amplification and analysis for preventing cross-contamination (Higuchi etal, (1992) Biotechnology, 10:413–17; Higuchi etal, (1993) Biotechnology, 11:1026–30; Holland etal, (1991) Proc. Natl. Acad. Sci., 88:7276–80).

The invention may be performed according to the 5' nuclease assay; the polymerase which conducts primer extension and amplifies the polynucleotide also possesses a 5' nuclease activity that serves to cleave the probe. A fluorescent "reporter" dye and a "quencher" may be attached at the 5' and 3' terminii to the SQP, which is complementary to the target DNA (Livak etal, U.S. Pat. No. 5,723,591). The dyes are selected and arranged to interact through a fluorescence resonance energy transfer (FRET) process (Clegg, R., (1992) Meth. Enzymol., 211:353–388). Alternatively, the reporter dye and quencher may be attached at internal positions on the probe, such as nucleobases, sugars, or internucleotide linkages. The reporter is a luminescent moiety that can be excited either by chemical reaction, producing chemiluminescence, or by light absorption, producing fluorescence (Livak etal, U.S. Pat. No. 5,876,930). Quantification of the amplicon results in deducing the number of target polynucleotide molecules present in the sample prior to amplification. The target polynucleotide may be a plasmid, a cDNA, a PCR product, genomic DNA, a restriction digest, or a ligation product. The target polynucleotide may be a mixture comprised of single nucleotide polymorphisms. The ABI PRISM™ 7700 Sequence Detection System performs the 5' nuclease assay, hybridization-based assays, and other quantification, fluorescent-based assays is (Applied Biosystems, Foster City, Calif.).

When the polymerase is thermostable and has 5' nuclease activity, the self-quenching fluorescence probes can be cleaved, i.e. digested, during amplification to separate said reporter dye from said quencher. The 5' nuclease assay of nucleic acid amplification employing reporter-quencher probes (Lee etal, (1993) Nucl. Acids Res., 21:3761–66; Livak etal, (1995) PCR Methods and Applications, 4:357–362) yields direct detection of polymerase chain reaction (PCR) products. The quencher is released from its close proximity to the reporter upon cleavage so that the signal from the reporter is no longer quenched. An increase in fluorescence occurs which correlates directly and proportionally with the increase in copies of the PCR product. The products of the nucleic acid amplification of the target polynucleotide and the external control polynucleotide may be measured and quantitated by end-point analysis or by real-time analysis.

The invention provides reporter-quencher probe assays with external fluorescence-generating controls to measure changes in fluorescence. Embodiments of the invention are useful for detecting low-copy number expression products, or low-frequency allelic discrimination tests. By using real-time or end-point analysis, detection and quantification of PCR products can be obtained by measuring the increase in fluorescence of cleaved, self-quenching fluorescent probes, or simply upon hybridization.

Positive amplification controls are to be distinguished from passive internal reference molecules (Livak etal, U.S. Pat. No. 5,736,333) which are added to PCR provide for signal and detection calibration and normalization. Passive internal references, such as non-complementary, reporter-quencher molecules do not hybridize to target or other polynucleotides, are not amplified, consumed or act as substrates for enzymes, and do not undergo chemical or enzymatic reactions of any sort. Thus, passive internal references do not provide verification or indication of conditions for amplification.

The methods of the present invention can also be conducted in hybridization-based assays where an increase in fluorescence is detected upon hybridization of a self-quenching fluorescence probe to target (Tyagi, etal, U.S. Pat. No. 5,925,517; Bagwell, EP 601889; Heller, etal EP 229943). Generally, an increase in fluorescence is proportional to the extent of amplification, i.e. the amount of amplicon produced during PCR. Cleavage of the probe by 5' nuclease activity of the polymerase need not occur. The invention may be practiced in some embodiments where the polymerase does not possess 5' nuclease activity.

Methods of the invention can be conducted by a high-throughput, data sampling routine during the course of PCR thermal cycling (real-time analysis) or at the end of PCR (end-point analysis). The sample format may be in the microtitre, microwell format, with 6 to 1536 wells. Each well may have a volume of 1 to 500 $\mu$l. The wells are arranged in equally-spaced dimensions, such as the common 96 well plate or tray with 8 rows of 12 wells, measuring approximately 3" by 4.5". Industry-standardized dimensions facilitate dispensing liquids with multi-tip pipettors, or programmed, liquid-delivery robots. The invention may also be practiced by spotting the reagents on an absorbent or porous material, frits, filters, or fibers which may be made of nylon, cellulose, polystyrene, etc. Alternatively, the reagents may be spotted on non-absorbent, planar surfaces such as glass or a polymer (Gilles, P. etal (1999) Nature Biotechnology, 17:365–70).

With calibrated, external controls, e.g. ECP1, ECP2, NTC (FIG. 5), the relative values of close concentrations can be resolved by factoring the history of the relative concentration values during the PCR. Genotyping by end-point analysis of the 5' nuclease assay is conducted on automated systems, e.g. an ABI PRISM® 7700 Sequence Detection System, Applied Biosystems) where the release of fluorescence is detected and measured by laser-induced fluorescence with an optical-fiber probe in a non-invasive, closed reaction chamber (Woudenberg etal, U.S. Pat. Nos. 5,928,907 and 6,015,674). Alternatively, multiple thermal cyclers, e.g. Models 9700, 9600, Applied Biosystems) can amplify the DNA before the cycled reactions are analyzed on where end-point detection measures fluorescence. The change in fluorescence, $\Delta$Rn, is the difference between the reporter fluorescence in the sample and that in the No Template Control (NTC). Rn is the emission intensity of a fluorescent reporter normalized to the emission of a passive reference (Rn=Emission intensity÷Emission intensity of passive reference).

Figure 6:
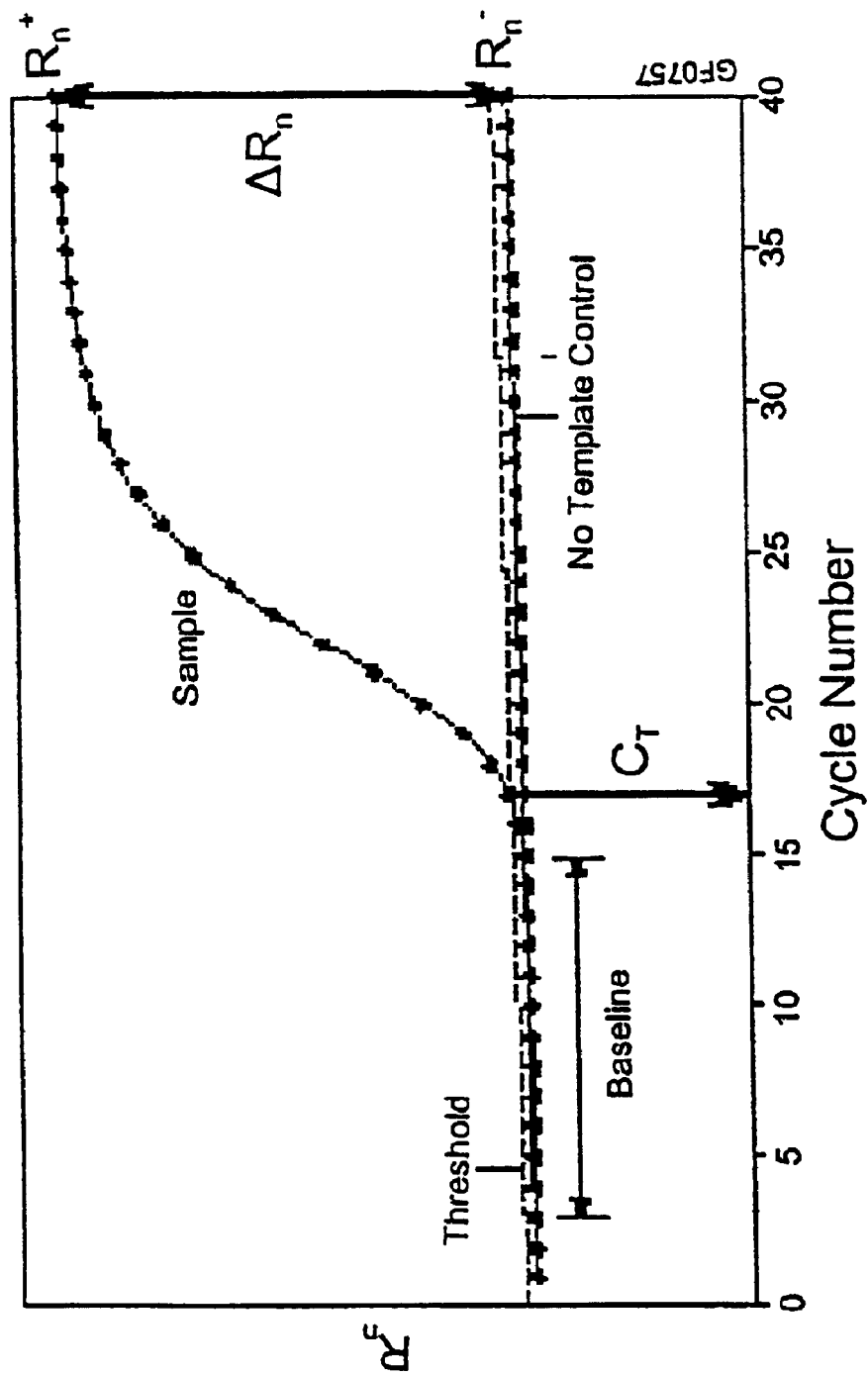
FIG. 6 shows an amplification plot of Rn versus cycle number, $C_T$.

During real-time analysis, the $\Delta$Rn is calculated during each PCR cycle. The threshold cycle, or $C_T$ value, is the PCR cycle at which a statistically significant increase in $\Delta$Rn is first detected, i.e. when the fluorescence ratio is distinguishable from the background. The optimum conditions are those that give the lowest $C_T$ value (FIG. 6). For a given reporter dye and a fixed concentration of target, both the Rn and $C_T$ values reflect the efficiency of the quencher.

V.4 Allelic Discrimination Assays

Allelic discrimination is the detection of different forms of the same gene that differ by nucleotide substitution, insertion, or deletion. The present invention provides novel methods for establishing external positive control data while detecting and discriminating alleles, including single nucleotide polymorphisms (SNP), during allele-specific PCR (Newton etal (1989) Nucleic Acids Res. 17:2503–16; Gibbs et al (1989) Nucleic Acids Res. 17:2437–48; TaqMan Allelic Discrimination Demonstration Kit Protocol, (1998) Applied Biosystems). In the 5' nuclease assay, DNA samples are genotyped for specific mutations, e.g. two alleles of single nucleotide polymorphisms (SNP). In this assay, each reaction contains two different self-quenching fluorescence probes, and each probe is labelled with a unique fluorescent dye.

Typically for allelic discrimination assays, in a first set of vessels, a target polynucleotide is amplified with primer extension reagents, which include a forward primer, a reverse primer, one or more detectable probes, a polymerase, and one or more nucleotide 5'-triphosphates. In a second set of vessels, a single-stranded external control polynucleotide, ECP1, is amplified with the primer extension reagents. In a third set of vessels, a second single-stranded external control polynucleotide, ECP2, is amplified with the primer extension reagents. The ECP are amplified with the same primers as target polynucleotide, giving detectable amplicons. A fourth set of vessels may contain only primer extension reagents, thus functioning as a negative control in which no amplification occurs. Any signal from the fourth set of vessels constitutes a background signal.

In allelic discrimination assays utilizing the 5' nuclease method and self-quenching probes, each SQP is complementary to one allele and hybridizes preferentially and with specificity to one of the alleles (FIGS. 2 and 3). In other words, for allelic discrimination, each allele associated with a target has a probe labelled with its own fluorescent dye. For example, FIG. 2 shows SQP1 with F1 reporter dye hybridizes to ECP1, and SQP2 with F2 reporter dye hybridizes to EDP2. The self-quenching fluorescence probes may contain two additional features that provide better allelic discrimination: (i) minor groove binder (MGB) labels enhances the discrimination between match and mismatch, i.e. better specificity ($\Delta$Tm), and thus allow the use of shorter probes, and (ii) non-fluorescent quenchers allow for better spectral discrimination between the reporter dyes and lower background fluorescence (User Bulletin, "Primer Express Version 1.5 and TaqMan MGB Probes for Allelic Discrimination", Applied Biosystems, May, 2000).

V.5 Gene Expression Assays

Gene expression assays may be practiced by the methods and kits of the invention, with real-time, quantitative detection of detectable probes. Genomic DNA target polynucleotides may be derived from human, drosophila, mouse, or other organisms. Patterns of gene expression may be monitored in response to various stimuli. Typically, a first set of vessels include the target polynucleotide samples and primer extension reagents. The primer extension reagents may include a forward primer, a reverse primer, a detectable probe, a polymerase, and one or more nucleotide 5'-triphosphates. A second set of vessels includes a single-stranded ECP and the same primer extension reagents as the first set of vessels. Another set of vessels contains only primer extension reagents and functions as a negative control.

V.6 Kits

Limiting the number of automated pipetting and dispensing steps minimizes errors and ambiguous results such as false positives and false negatives may severely reduce the value of the PCR-based procedure. To practice some embodiments of the invention, a kit of reagents may be configured for nucleic acid amplification. An exemplary kit may include: a single-stranded external control polynucleotide, a forward primer, a reverse primer, a nucleic acid polymerase having 5' nuclease activity, a detectable probe such as an SQP, one or more nucleotide 5'-triphosphates; and other primer extension reagents necessary for nucleic acid amplification such as a buffer. An example of a suitable nucleic acid amplification buffer for dissolution of kit reagents is: 10 mM Tris (pH 8.4), 50 mM KCl, 1.5 mM MgCl$_2$, 0.01% gelatin, 0.01% NP40, and 0.01% Tween™.

In one embodiment, the primers, probes and primer extension reagents are conveniently dispensed as a kit of reagents. Amplification of an ECP with a kit containing primers and probes affirmatively verifies that the primers and probes were manufactured and dispensed (mixed) correctly. Thus, certain embodiments of kits allow for quality control of PCR assays. Quality control ensures that the primer extension reagents are capable of detecting the target polynucleotide. Dispensing includes automated, robotic delivery to wells, spots, and other types of vessels. Multiple kits of the invention can be assembled and delivered by dispensing to an array configuration for amplification. Each kit may include different detectable probes and primers. Target polynucleotides and ECP can be separately dispensed to various vessels in the array to achieve many possible amplification tests, including positive and negative controls. Negative controls are achieved by withholding any target or ECP. Amplification of an ECP will provide verification of the correct delivery of the correct kit reagents to the correct location, i.e. vessel.

Reagents in a kit format may be formulated at optimal concentrations, ready for efficient and automated dispensing into large numbers of sample vessels or wells. One kit embodiment may be a mixture of a set of forward primer, reverse primer, and two SQP. Such a kit may be specific for amplification of a known allele site or SNP. Each SQP may be a perfect complement to an allelic form.

V.7 Examples

The invention will be further clarified by a consideration of the following examples, which are intended to be purely exemplary of the present invention and not to in any way limit its scope.

Example 1

Preparation of Self-quenching Fluorescence Probes

Self-quenching probes were prepared by automated synthesis (Model 394 DNA/RNA synthesizer, Applied Biosystems) according to the general procedures described in the users manual. A 5' FAM, 3' TAMRA probe can be synthesized at 0.2 $\mu$mol scale using TAMRA-labelled CPG solid supports for 3' labelling (Mullah et al, (1997) Tetrahedron Letters, 38: 5751–5754; Mullah et al, (1998) Nucl. Acids Res. 26:1026–1031), the set of phosphoramidite nucleosides $A^{bz}$, $G_{dmf}$, $C^{bz}$, T, other reagents recommended by the manufacturer (Applied Biosystems) and FAM dye-labelled phosphoramidite for 5' labelling (Theisen et al (1992) "Fluorescent dye phosphoramidite labelling of oligonucleotides", in *Nucleic Acid Symposium Series No. 27*, Oxford University Press, Oxford, pp. 99–100). The standard 0.2 $\mu$mol synthesis cycle was slightly modified by extending coupling time of FAM amidite by an additional 120 seconds.

After completion of the synthesis, oligonucleotides labelled with a reporter dye attached to a 5'-end of and a quencher located at a 3'-end were autocleaved from the support on the DNA synthesizer by treating with a mixture of MeOH:t-BuNH$_2$:H$_2$O (1:1:2) (Woo et al, U.S. Pat. No. 5,231,191) for a 1 hr autocleavage procedure as described in the users manual for the Applied Biosystems Model 394 DNA/RNA synthesizer. Base protecting groups were removed by heating the mixture at 85° C. for 1 hr or at 65°

C. for 3 h. The oligonucleotides can be analyzed and purified by reverse phase HPLC, anion-exchange HPLC, capillary gel electrophoresis, polyacrylamide gel electrophoresis, and other conventional techniques (Andrus (1992) in *Evaluating and Isolating Synthetic Oligonucleotides*, Applied Biosystems, Inc.).

Example 2

Allelic Discrimination Assay

Experiments were performed with the ABI PRISM® 7700 Sequence Detector at a 25-μL final reaction volume per sample The following kit of reagents were designed to provide 200 reactions of 50 μL each:

TaqMan® Universal PCR Master Mix—5.75 mL total, sufficient for 200 reactions of 50 μL each, containing the following: Tris-HCl pH 8.0, 100 mM, 16% glycerol, 0.1% gelatin, 0.02%, Tween 20™, 10 mM $MgCl_2$, 400 μM each of dATP, dCTP, 7-deaza-dGTP and 800 μM of dUTP, 0.1 U/μl of AmpliTaqGold DNA polymerase, 0.02 U/μl of Amperase UNG, and 120 nM of Passive Reference (Applied Biosystems)

Probe and Primer Mix—3.45 mL total, sufficient for 200 reactions of 50 μL each, containing the following:

```
Forward primer, 20µM:
5'-CAG TGG TGC CAG CTC AGC A-3'                                                          SEQ.
                                                                                         ID
                                                                                         NO.1

Reverse primer, 20µM:
5'-GGT GAG GCT GTG GCT GAA CA-3'                                                         SEQ.
                                                                                         ID
                                                                                         NO.2

Self-quenching fluorescence probe 1, 10µM:
5'-TET-CCA GCA ACC AAT GAT GCC CGT T-TAMRA-3'                                            SEQ.
                                                                                         ID
                                                                                         NO.3

Self-quenching fluorescence probe 2, 10µM:
5'-FAM-CCA GCA AGC ACT GAT GCC TGT TC-TAMRA-3'                                           SEQ.
                                                                                         ID
                                                                                         NO.4

ECP1 250 µL (10 fg/µL), sufficient for 100 reactions:
5' TAG GTG AGG CTG TGG CTG AAC AAT AAC GGG CAT CAT TGG TTG CTG GGC TGC TGA GCT GGC ACC ACT GCC 3'   SEQ.
                                                                                         ID
                                                                                         NO.5

ECP2 250 µL (10 fg/µL), sufficient for 100 reactions:
5' TAG GTG AGG CTG TGG CTG AAC AAT GAA CAG GCA TCA GTG CTT GCT GGG CTG CTG AGC TGG CAC CAC TGC C 3' SEQ
                                                                                         ID
                                                                                         NO.6
```

Genomic control DNA 1.0 mL (10 ng/μL), sufficient for 200 reactions.

Control and sample reactions were prepared according to the plate diagram of FIG. 5 in a standard 96-well reaction plate with the following volumes of reagents:

| | | |
|---|---|---|
| A1–A8 | NTC | 220 μL of 2X Master Mix, 132 μL of Probe and Primer Mix, and 88 μL of TE buffer (10 mM Tris-HCl, 1 mM EDTA, pH 8.0) were mixed. 50 μL of the mixture was delivered to each of the 8 wells. |
| A9–A12 B1–B4 | ECP1 | 220 μL of 2X Master Mix, 132 μL of Probe and Primer Mix, 44 μL of ECP1, and 44 μL of TE buffer were mixed. 50 μL of the mixture was delivered to each of the 8 wells. |
| B5–B12 | ECP2 | 220 μL of 2X Master Mix, 132 μL of Probe and Primer Mix, 44 μL of ECP2, and 44 μL of TE buffer were mixed. 50 μL of the mixture was delivered to each of the 8 wells. |
| C1–H12 | sample unknowns (UNK) | 2000 μL of 2X Master Mix, 1200 μL of Probe and Primer Mix, 400 μL of Genomic Control DNA, and 400 μL of TE buffer were mixed. 50 μL of the mixture was delivered to each of the 72 wells. |

The plate of prepared samples were thermal cycled to conduct PCR in a thermal cycler (GeneAmp PCR System 9600, 9700, and ABI Prism 7700 Sequence Detector, Applied Biosystems) according to the following program: (a) 2 minute hold at 50° C., (b) 10 minute hold at 95° C., and (c) 40 cycles of 15 seconds at 95° C. to melt then 1 minute at 62° C. to anneal and extend.

Figure 7:
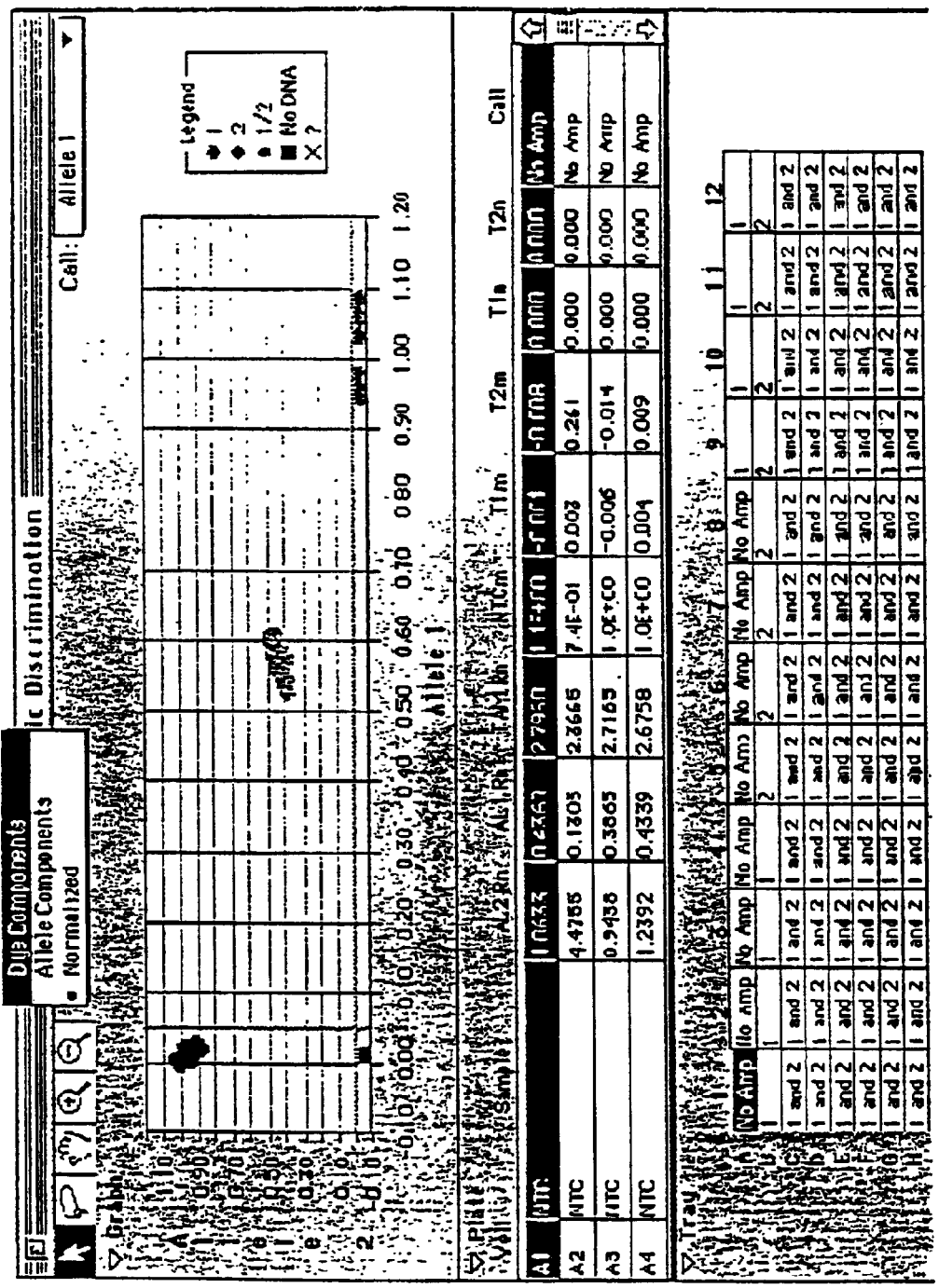
FIG. 7 shows clustering of data in the allelic discrimination assay of Example 1. The fluorescent signals from FAM- and TET-labelled self-quenching fluorescence probes in each reaction are plotted.

Data was collected by real-time detection on the ABI Prism 7700 and normalized for each allele. Fluorescence values at the Emission max for FAM 1 and TET 2 were measured for each sample in each well. A genotype call from the Genomic control DNA samples (UNK) was made for Allele 1 (homozygote 1), Allele 2 (homozygote 2), or Allele ½ (heterozygote). The fluorescent reporter dye (TET, Em. max 538 nm) on the allele 1 probe is spectrally resolved from the dye (FAM, Em. max 518 nm) on the allele 2 probe (FIG. 7).

All publications cited herein are incorporated by reference, and to the same extent as if each individual publication was specifically and individually indicated to be incorporated by reference.

Although only a few embodiments have been described in detail above, those having ordinary skill in the molecular biology art will clearly understand that many modifications are possible in the illustrated embodiments without departing from the teachings thereof. All such modifications are intended to be encompassed within the following claims.

We claim:

1. A kit of reagents for nucleic acid amplification comprising:

a single-stranded external control polynucleotide, a forward primer, a reverse primer, a polymerase, a detectable probe, and one or more nucleotide 5'-triphosphates;

wherein the forward primer and the detectable probe are separated by 0 to 5 macleotides when hybridized to the external control polynucleotide, or its complement, and the reverse primer and the detectable probe are separated by 0 to 5 nucleotides when hybridized to the external control polynucleotide, or its complement.

2. The kit of claim 1 wherein the forward primer and reverse primer are each 10 to 40 nucleotides in length.

3. The kit of claim 1 wherein the single-stranded external control polynucleotide is 30 to 110 nucleotides in length.

4. The kit of claim 1 wherein the single-stranded external control polynucleotide is 50 to 70 nucleotides in length.

5. The kit of claim 1 wherein the external control polynucleotide, or its complement, forms single-stranded overhangs consisting of 1 to about 10 nucleotides when hybridized to the forward primer or to the reverse primer.

6. The kit of claim 1 wherein said polymerase is a thermostable polymerase with 5' nuclease activity.

7. The kit of claim 1 wherein the detectable probe comprises a fluorescent dye.

8. The kit of claim 1 wherein the detectable probe is a self-quenching fluorescence probe comprising a reporter dye and a quencher.

9. The kit of claim 8 wherein the self-quenching fluorescence probe is 10 to 40 nucleotides in length.

10. The kit of claim 8 wherein said reporter dye is a xanthene dye.

11. The kit of claim 10 wherein said xanthene dye is a fluorescein dye.

12. The kit of claim 11 wherein said fluorescein dye is selected from the group consisting of:

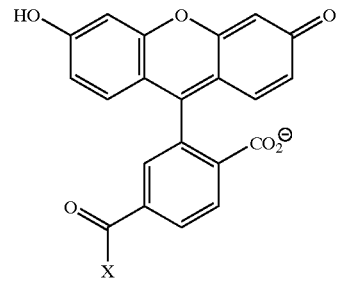

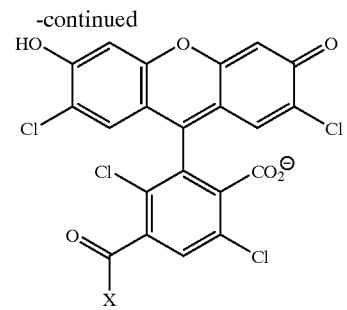

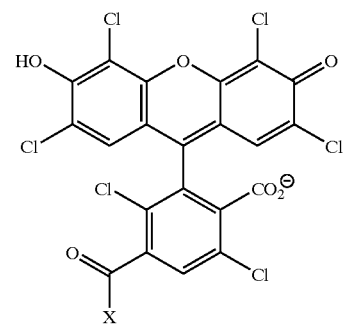

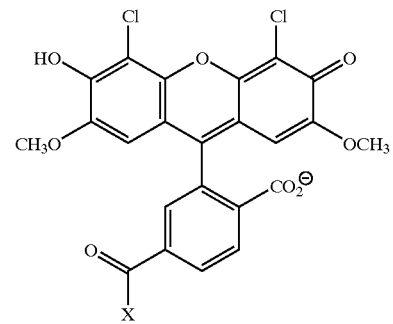

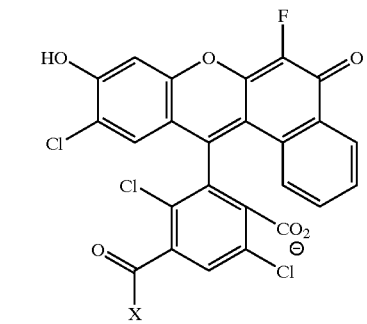

-continued

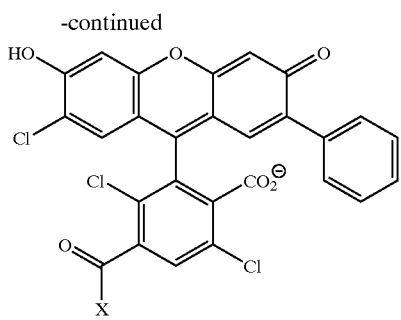

where X is an attachment site to the probe.

13. The kit of claim 8 wherein said quencher is selected from the group consisting of:

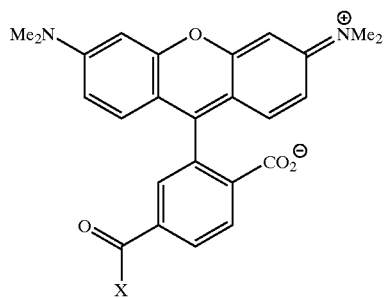

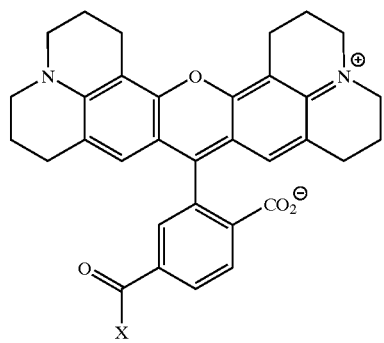

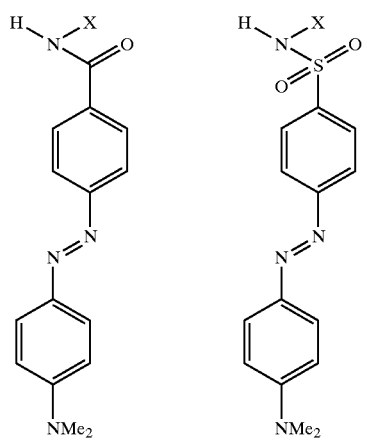

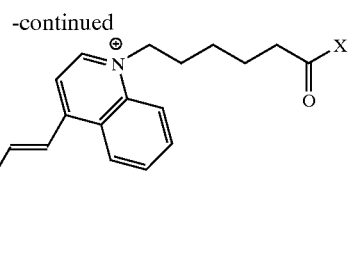

where X is an attachment site to the probe.

14. The kit of claim 8 wherein said reporter dye is separated from said quencher by at least 12 nucleotides.

15. The kit of claim 8 wherein said reporter dye is attached at a 5' terminus or a 3' terminus of the self-quenching fluorescence probe.

16. The kit of claim 8 wherein said quencher is attached at a 5' terminus or a 3' terminus of the self-quenching fluorescence probe.

17. The kit of claim 8 wherein said quencher is non-fluorescent.

18. The kit of claim 1 wherein the detectable probe is labelled with a minor groove binder.

19. The kit of claim 8 wherein the self-quenching fluorescence probe is labelled with a minor groove binder.

20. The kit of claim 8 wherein the self-quenching fluorescence probe is labelled with a minor groove binder at a 3' terminus nucleotide.

21. The kit of claim 19 wherein the minor groove binder has the structure:

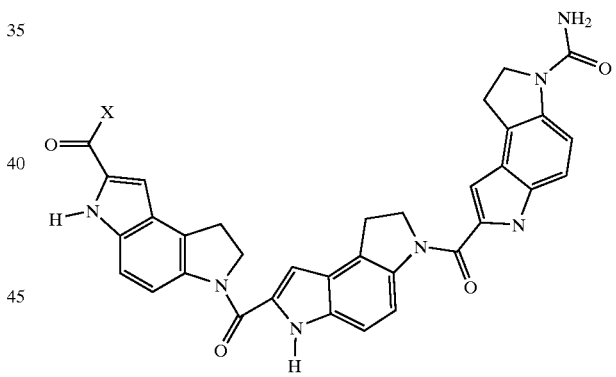

where X is an attachment site to the probe.

22. The kit of claim 1 where one or more nucleotide 5'-triphosphates comprises a fluorescent dye, a quencher, biotin, or a minor groove binder.

23. The kit of claim 8 further comprising a second self-quenching fluorescence probe comprising a reporter dye and a quencher wherein the sequences of the first self-quenching fluorescence probe and second self-quenching fluorescence probe differ by a single nucleotide.

24. The kit of claim 1 wherein the concentration of the forward primer and the concentration of the reverse primer is each about 10 to 100 $\mu$M, the concentration of each nucleotide 5'-triphosphate is about 100 to 1000 $\mu$M, and the concentration of the self-quenching fluorescence probe is about 1 to 100 $\mu$M.

25. The kit of claim 1 further comprising a second single-stranded external control polynucleotide wherein the forward primer and the detectable probe are separated by 0 to 5 nucleotides when hybridized to the second external control polynucleotide, or its complement, and the reverse primer and the detectable probe are separated by 0 to 5 nucleotides when hybridized to the external control polynucleotide, or its complement; and wherein the sequence complementary to the detectable probe of the first single-stranded external control polynucleotide differs from the sequence complementary to the detectable probe of the second single-stranded external control polynucleotide by one or more nucleotides, nucleotide insertions, or nucleotide deletions.

26. The kit of claim 1 where the reagents are delivered by robotic means to one or more vessels.

27. The kit of claim 26 where the reagents are spotted on an absorbent or porous material.

28. The kit of claim 26 where the reagents are spotted on a non-absorbent and planar surface.

29. The kit of claim 26 wherein the reagents are located in an array configuration having 6 to 1536 reaction sites.

30. The kit of claim 29 wherein the reagents are located in a microwell tray having 96 to 384 wells.

31. The kit of claim 30 wherein each well has a volume from 1 to 500 $\mu$l.

* * * * *

UNITED STATES PATENT AND TRADEMARK OFFICE
CERTIFICATE OF CORRECTION

PATENT NO.         : 6,890,718 B2                                       Page 1 of 1
APPLICATION NO. : 10/099738
DATED              : May 10, 2005
INVENTOR(S)        : Christian A. Heid et al.

It is certified that error appears in the above-identified patent and that said Letters Patent is hereby corrected as shown below:

Column 21, Claim 1, line 21, please delete, "macleotides" and insert --nucleotides--.

Signed and Sealed this

Twenty-first Day of November, 2006

JON W. DUDAS
*Director of the United States Patent and Trademark Office*

SEQUENCE LISTING

<160> NUMBER OF SEQ ID NOS: 6

<210> SEQ ID NO 1
<211> LENGTH: 19
<212> TYPE: DNA
<213> ORGANISM: Unknown Organism
<220> FEATURE:
<223> OTHER INFORMATION: Description of Unknown Organism: test sequence

<400> SEQUENCE: 1
cagtggtgcc agctcagca                                             19

<210> SEQ ID NO 2
<211> LENGTH: 20
<212> TYPE: DNA
<213> ORGANISM: Unknown Organism
<220> FEATURE:
<223> OTHER INFORMATION: Description of Unknown Organism: test sequence

<400> SEQUENCE: 2
ggtgaggctg tggctgaaca                                            20

<210> SEQ ID NO 3
<211> LENGTH: 22
<212> TYPE: DNA
<213> ORGANISM: Unknown Organism
<220> FEATURE:
<223> OTHER INFORMATION: Description of Unknown Organism: test sequence

<400> SEQUENCE: 3
ccagcaacca atgatgcccg tt                                         22

<210> SEQ ID NO 4
<211> LENGTH: 23
<212> TYPE: DNA
<213> ORGANISM: Unknown Organism
<220> FEATURE:
<223> OTHER INFORMATION: Description of Unknown Organism: test sequence

<400> SEQUENCE: 4
ccagcaagca ctgatgcctg ttc                                        23

<210> SEQ ID NO 5
<211> LENGTH: 69
<212> TYPE: DNA
<213> ORGANISM: Unknown Organism
<220> FEATURE:
<223> OTHER INFORMATION: Description of Unknown Organism: test sequence

<400> SEQUENCE: 5
taggtgaggc tgtggctgaa caataacggg catcattggt tgctgggctg ctgagctggc    60
accactgcc                                                           69

<210> SEQ ID NO 6
<211> LENGTH: 70
<212> TYPE: DNA
<213> ORGANISM: Unknown Organism
<220> FEATURE:
<223> OTHER INFORMATION: Description of Unknown Organism: test sequence

<400> SEQUENCE: 6

-continued

```
taggtgaggc tgtggctgaa caatgaacag gcatcagtgc ttgctgggct gctgagctgg    60
caccactgcc                                                            70
```